United States Patent
Kendall et al.

(10) Patent No.: US 6,646,076 B1
(45) Date of Patent: Nov. 11, 2003

(54) INTERNALLY BLOCKED ORGANOBORATE INITIATORS AND ADHESIVES THEREFROM

(75) Inventors: Jonathan L. Kendall, Apex, NC (US); Robin F. Righettini, Apex, NC (US); Kirk J. Abbey, Raleigh, NC (US)

(73) Assignee: Lord Corporation, Cary, NC (US)

(*) Notice: Subject to any disclaimer, the term of this patent is extended or adjusted under 35 U.S.C. 154(b) by 0 days.

(21) Appl. No.: 10/397,007

(22) Filed: Mar. 25, 2003

Related U.S. Application Data (62) Division of application No. 10/008,239, filed on Nov. 6, 2001.

(51) Int. Cl.[7] .................................... C08F 4/12
(52) U.S. Cl. ............ 526/195; 526/196; 526/204; 526/352; 526/351; 526/242; 526/302; 526/344; 526/191; 526/319; 526/285; 156/325; 156/327
(58) Field of Search ................. 526/195, 196, 526/204, 352, 351, 242, 302, 344, 191, 319, 285; 156/325, 327

(56) References Cited

U.S. PATENT DOCUMENTS 3,163,679 A * 12/1964 Koster et al.
4,525,309 A 6/1985 Matteson et al.
5,690,780 A * 11/1997 Zharov et al. ............... 156/332

OTHER PUBLICATIONS

Lieu, et al.: "Cyclic Hydroborate Complexes of Metallocenes IV" *Inorganic Chemistry* No. 38, Apr. 14, 1999, pp. 2169–2173.

Bai, et al: "Reactions of Borinic Esters with (1,1–Dichloroalkyl)Lithium. A Facile Synthesis of Teriary Carbinols" *Journal of Organometallic Chemistry.*, vol 367, No. 3, 1989, pp. c9–c11.

* cited by examiner

Primary Examiner—David W. Wu
Assistant Examiner—William Cheung
(74) Attorney, Agent, or Firm—Miles B. Dearth

(57) ABSTRACT

Disclosed are internally blocked borates useful for polymerizable compositions, and polymerizable adhesives made therewith. The internally blocked borates have general structures:

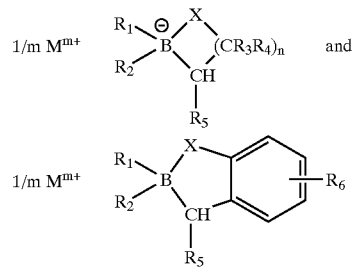

wherein X represents —$CHR_6$—, oxygen or sulfur; n is an integer; $R_1$, $R_2$, $R_3$, $R_4$, $R_5$, and $R_6$ are independently selected, for example, from unsubstituted and substituted $C_1$–$C_{10}$ alkyl, alkylene groups, or aryl groups, including other embodiments further defined, and M is a counter ion with positive charge m.

18 Claims, 2 Drawing Sheets

Rate of Strength Development on Polypropylene Lap Shear Samples

INTERNALLY BLOCKED ORGANOBORATE INITIATORS AND ADHESIVES THEREFROM

This application is a divisional of pending U.S. patent application Ser. No. 10/008,239, filed Nov. 6, 2001.

FIELD OF THE INVENTION

The invention is directed to novel internally blocked organoborates having utility in the initiation of addition polymerizable monomers. The invention pertains also to adaptations for adhesives, with particular reference to polymerizable acrylic adhesive systems.

BACKGROUND OF THE INVENTION

Typical conventional reactive acrylic adhesives utilize well known non-borate free radical initiators. U.S. Pat. No. 4,348,503 discloses acrylic adhesives initiated by a dibasic acid perester and a metal ion. U.S. Pat. No. 4,081,308 discloses an acrylic adhesive initiated with a saccharin salt and α-hydroxysulfone. U.S. Pat. No. 4,331,795 discloses an acrylic adhesive cured with hydroperoxide, thiourea and a metal salt. The non-borate initiated reactions for the above adhesives are inhibited by oxygen.

Organoborane free-radical initiation has been reported in the literature. See, for example, Bawn, C. E. H., Margerison, D. and Richardson, N. M., Proc. Chem. Soc., 1959, 397–398; Furukawa, J., Tsuruta,T., J. Polym. Sci., 1958, 28, 727–729; Dotty, P. M., Fouss, R. M., Mark, H., Overberger, C. G. and Smets, G. J. Polym. Sci. 1958, 33, 502–504. Two mechanisms of the oxygen-organoborane reaction have been postulated. Mirviss, S. B., J. Am. Chem. Soc. 1961, 83, 3051–3056; Davies, A. G., Roberts, B. P., J. Chem. Soc. B, 1969, 311–317; Allies, P. G., Brindly, P. B., J. Chem. Soc. B. 1969, 1126–1131. One mechanism involves the homolytic cleavage of the oxygen-oxygen bond to generate an alkoxy radical and a dialkyl boratoxy radical. The other major pathway is believed to involve homolytic cleavage of the alkyl-oxygen bond to form an alkyl radical and a dialkyl boraperoxy radical. The alkyl radical may react with more oxygen to produce an alkylperoxy radical, which may then react with organoborane to regenerate the alkyl radical and the borane peroxide. Thus one of the advantages in the use of organoborane initiated reactions is that atmospheric oxygen can be used as the source for the co-initiator in the formation of radicals.

Approaches to control the reactivity of organoboranes are known. E. Frankland reported the synthesis of triethylborane and its air-stable complex with a Lewis base, e.g., ammonia. Phil. Trans. Royal Soc. Vol. 152, pp. 167–183 (1863). The air-stable amine complex is believed to slow down the oxidation of organoboranes by blocking the borane open site for oxygen binding, which is the first step in the reaction of organoboranes with oxygen. The initiator can thus be stored in the blocked state and then de-blocked with an appropriate de-blocking or de-complexing agent, such as a stronger Lewis acid.

British Patent Specification No. 1,113,722 entitled "Aerobically Polymerisable Compositions," published May 15, 1968 discloses a polymerizable composition adapted as a structural adhesive and containing acrylic monomer(s) and an peroxide-activated triaryl, e.g., triphenylborane, complex with hydroxide, ammonia, benzene, or an amine. The polymerization is activated by heating or the addition of an acid. The resulting compositions are reportedly useful as adhesives.

Japanese Patent App. 69-100477 discloses a simple adhesive containing methyl methacrylate, tributylborane, and PMMA for use in the bonding of polyolefins or vinyl polymer articles. Excellent tensile shear strengths of over 1800 p.s.i. were reported. Acrylic adhesives polymerized with tributylborane and other trialkylboranes were reported during the 1970's. (See, U.S. Pat. No. 3,527,737 to Masuhara, et al. and GDR Pat. No. 2,321,215 to Masuhara, et al.)

Two-part adhesives utilizing in one part trialkyl-, triphenyl-, or alkylphenylborane blocked with a primary or secondary amine and in the other part an organic acid or aldehyde are reported in U.S. Pat. No. 5,106,928, Can. Patent No. 2,061,021, U.S. Pat. No. 5,143,884, U.S. Pat. No. 5 310 835, and U.S. Pat. No. 5,376,746.

U.S. Pat. Nos. 5,539,070, 5,690,780 and 5,691,065 disclose polyoxyalkylenepolyamine-blocked organoborane initiator, with a nitrogen to boron ratio of 1:1 to 1.5:1 useful for adhesives to bond low surface energy materials such as polyolefins and polytetrafluoroethylene.

Organoborane alkoxide complexes are known but there is little reported literature. See, Ludman, C. J.; Waddington, T. C. J. Chem. Soc. A 1966, 1816–1819 and *Angew. Chem. Int Ed. Engl.* 1972, 11, 48–49. A combination of potassium methoxide with triethyl borane resulted in the isolation of the hygroscopic white solid potassium triethylmethoxy borate(III). Similarly, the synthesis of tetraalkylborates, such as sodium tetraethylborate(III) are known.

Honeycutt, Jr,. J. B., Riddle, J. M., J. Am. Chem. Soc. 1961, 83, 369–373. The present inventors have shown that these tetraalkylborates are effective as initiators for acrylic adhesives with or without a deblocking agent. The particular advantage of these initiators over amine-blocked boranes is their tendency to remain colorless after cure. In contrast, amine-blocked borane initiated acrylic adhesives yellow with time.

Hydroxy and/or alkoxy complexing agents for organoborane initiators are described in WO 01/32716, published May 10, 2001. The complexed initiator has the following structure:

wherein $R^1$ is alkyl $C_{1-10}$, $R^2$ and $R^3$ are alkyl or phenyl and Cx is an alkoxide, or hydroxide and the value of v is selected so as to provide an effective ratio of oxygen atoms of the alkoxides and/or hydroxides to boron atoms in the complex. Mixtures of hydroxide complexes with alkoxide complexes are suggested. One alkoxide blocking group is illustrated as where $R^4$ is independently selected from hydrogen or an organic group, e.g. alkyl or alkylene, $M^{(m+)}$ is a group IA, IIA, or ammonium countercation, n is an integer >0, and m is an integer >0. An organoborane complex having the following structure follows from this:

It has been observed that cured polymerizable adhesives initiated with amine-blocked boranes begin to turn yellow due to the presence of the amine group. In contrast, the decomposition products of alkoxy-blocked organoborates (alcohols) and alkyl-blocked organoborates (alkanes) do not undergo the unfortunate yellowing with time. The avoidance of discoloration of the cured bond line is important where a bond line must appear on a visually accessible surface of a bonded article for acceptable aesthetics.

There are numerous considerations in the replacement of mechanically fastened articles with adhesive bonding. It has been observed that conventional alkoxyborates have relatively poor air stability. For example when sodium ethoxotriethylborate(III) is exposed to air for 24 hours, the borate loses 46% of its mass and becomes inactive, unable to initiate the polymerization of methacrylate monomers. Air stability is important for meeting the practical problems in the commercial manufacturing and packaging of formulated borane-containing adhesive systems.

Another requirement for practical application of adhesives systems is the control of open time. Open time refers to the ability of an adhesive to cure providing strong bonds after exposure to air. Amine blocked boranes are known to have open times of a matter of minutes. A blocked boron-based initiator having an open time beyond a few minutes would be of industrial importance.

The inventors have discovered a class of 4-coordinate borates where at least two of the coordinates form part of a ring and have surprisingly good air stability enabling their use in packaged two-part polymerizable adhesives. As illustrated below, internally blocked borates exhibit stability in air of several days and retain an ability to cure methacrylate monomers. Moreover, the internally blocked borate initiators of the present invention remain colorless after curing, whereas conventional amine complexed borates are known to exhibit yellowing after curing.

SUMMARY OF THE INVENTION

In accordance with one aspect of the invention, novel 4-coordinate internally blocked borates are disclosed. The heterocycles have as part of the internal ring structure boron and oxa- or thia-moieties. These borates exhibit unexpected stability in the blocked state, ready reaction with de-blocking agents, and rapidly initiate polymerization in the unblocked state. The novel internally blocked heterocyclic borates have the structures (I) and (I'):

wherein for (I) and (I') X is oxygen or sulfur; when X represents oxygen, n is the integer 2, 3, 4, or 5; when X represents sulfur, n is the integer 1, 2, 3, 4 or 5; $R_1$, $R_2$, $R_3$, $R_4$, $R_5$ and $R_6$ are, independently, substituted or unsubstituted alkyl or alkylene groups containing 1 to 10 carbon atoms, substituted aryl groups having up to 7 to 12 carbon atoms, or unsubstituted aryl groups; $R_3$, $R_4$, $R_5$ and $R_6$ in (I) can be hydrogen; $R_1$ and $R_2$ in (I) and (I') can be part of a second unsubstituted or substituted cyclic borate; $R_1$ and $R_2$ in (I) and (I') can comprise a spiro ring or a spiro-ether ring; $R_1$ or $R_2$ together with $R_3$ or $R_4$ in (I) can be linked to form a cycloaliphatic ring; or $R_1$ or $R_2$ together with either $R_3$ or $R_4$ in (I) can comprise a cyclic ether ring; and M is any positively charged species with m being greater than 0.

In another aspect of the invention, two-part addition curing adhesives are provided where one part contains a 4-coordinate internally blocked borate according to (II) and (II')

wherein for (II) and (II') X represents —$CHR_7$—, oxygen or sulfur; n is the integer 1, 2, 3, 4, or 5. $R_1$, $R_2$, $R_3$, $R_4$, $R_5$, $R_6$ and $R_7$ are independently selected from substituted or unsubstituted alkyl or alkylene groups containing 1 to 10 carbon atoms, substituted aryl groups having up to 7 to 12 carbon atoms, and unsubstituted aryl groups. $R_3$, $R_4$, $R_5$, $R_6$ and $R_7$ can be hydrogen; $R_1$ and $R_2$ in (I), (I'), (II) and (II') can be part of a second unsubstituted or substituted cyclic borate, or $R_1$ and $R_2$ can comprise a spiro ring or a spiro-ether ring; or $R_1$ or $R_2$ together with $R_3$ or $R_4$ in (I) and (II) can be linked to form a cycloaliphatic ring; or $R_1$ or $R_2$ together with either $R_3$ or $R_4$ in (I) and (II) can comprise a cyclic ether ring; and M is any positively charged species with m being greater than 0.

Internal blocking refers to the presence of boron being part of the internal ring structure bridged across at least two of the four boron coordinates or valences. A critical requirement is met in that the internally blocked borates according to (I), (I'), (II) and (II') have considerable stability of initiator activity after exposure to air. Additionally, they provide a rapid rate of polymerization of addition polymerizable monomers upon contact with a deblocking agent and the presence of air. The rapid polymerization rate enables improved formation of structural adhesive bonds. The unexpected stability in the blocked state, ready reaction with de-blocking agents, and rapid initiation of polymerization in the unblocked state provide shelf stability so that adhesives can be packaged in conventional containers, for example multi-part or multi-chamber cartridges.

In accordance with the invention there is provided a two-part oxygen-promoted adhesive, where a first part comprises a polymerizable component and an optional deblocking agent, an optional accelerator which is either another more reactive borane initiator or a non-borane initiator; and the second part comprises the internally blocked borate (II) or (II') and a carrier liquid. The adhesive preferably contains monomer and/or oligomer or polymer components in either or both of the first and/or second parts. The preferred optional accelerator is a non-borane containing free radical initiator.

In accordance with the adhesive methods according to the invention there is provided a method for adhesively bonding two substrates together to form a bonded composite, the method to form the composite comprising the steps of:
- (a) providing a first substrate and a second substrate that is the same material or a different material from the first substrate;
- (b) applying to the first and/or second substrate the following materials in a mixture:
  - (i) at least one polymerizable component;
  - (ii) an effective amount of an internally blocked organoborate (II) or (II');

optionally (iii) an activating or deblocking agent, optional accelerator and/or optional non-borane free radical initiator; and
- (c) mating the first and second substrates with the components of step (b) therebetween; and
- (d) allowing the at least one polymerizable component to polymerize, at ambient conditions or with the optional application of heat, whereby the first and second substrates are adhesively bonded together.

In another aspect the invention relates to applying a primer prior to a method of bonding comprising applying a solution of the internally blocked organoborate (II) or (II') in an inert organic solvent followed by treatment of at least one substrate with the polymerizable composition.

DETAILED DESCRIPTION OF THE PREFERRED EMBODIMENTS

The term "internally blocked" in reference to the organoborates herein means a four coordinate boron atom being part of an internal ring structure bridged across two of the four boron coordinates or valences. Internal blocking includes a single ring or a two-ring structure where boron is part of one or multi-ring structures. An internally blocked organoborate is readily distinguished from known cyclic borates where the ring structure is bonded to boron through one coordinate atom. Cyclic amine complexed borates of this sort are disclosed in WO 01/44311 A1, published, Jun. 21, 2001.

The term "air stability" means not only that there is no pyrophoric tendency, there is an ability of the internally blocked borate to retain initiator function after exposure to ambient air over several days to several weeks in the blocked state.

In accordance with structures (I), (I'), (II) and (II'), wherein for (1) and (I') X=O, or S, and in structures (II) and (II') X=—CHR$_7$—, oxygen or sulfur, the substituents R$_1$, R$_2$, R$_3$, R$_4$, R$_5$, R$_6$ and R$_7$ in any instance are hydrocarbyl, including substituted or unsubstituted C$_1$–C$_{10}$ alkyl, hydroxyhydrocarbyl, hydrocabyl ether groups containing one or more than one oxygen atoms; substituted C$_1$–C$_{10}$ hydrocarbyl, oxyhydrocarbyl or hydrocarbyl ether groups. Specific examples include but are not limited to, methyl, ethyl, methoxybutyl-, ethoxyethyl-, propyl, butyl, butoxybutyl-, pentyl, hexyl, heptyl, octyl, nonyl, decyl; such as isopropyl, isopropoxypropyl-, isobutyl, isobutoxyethyl-, methoxypropyl-; unsubstituted aryl groups, and substituted aryl groups containing 7 to 12 carbon atoms. R$_1$ and R$_2$ can be part of an unsubstituted or substituted ring structure containing from 4 to 10 carbon atoms in the ring. At least two of R$_3$, R$_4$, and R$_5$ in (I) and (II) can be linked in one or more ring structures (as in Example 11), or R$_3$, R$_4$, and R$_5$ in (I) and (II) can be arranged with a spiro alkylene ring (as in Ex. 13); (CR$_3$R$_4$)$_n$ in (I) and (II) can be part of the internal ring structure such as illustrated in (I' and II') and shown in Example 13, (CR$_3$R$_4$)$_n$ in (I) and (II) can be part of a spiro - ether ring structure as in Example 14; and R$_1$ or R$_2$ and R$_3$ or R$_4$ (I) and (II) can be linked in a ring structure linking R$_1$ with either R$_3$ or R$_4$ or linking R$_2$ with either R$_3$ or R$_4$, and R$_1$ or R$_2$ and R$_3$ or R$_4$ (I) and (II) can be linked in a cyclic ether ring structure linking R$_1$ with either R$_3$ or R$_4$ or linking R$_2$ with either R$_3$ or R$_4$.

Substituent groups on R$_1$, R$_2$, R$_3$, R$_4$, R$_5$, R$_6$ and/or R$_7$ are preferably selected so that they do not tend to de-complex the borate. Generally the substituents for the hydrocarbyl, oxyhydrocarbyl and hydrocarbyl ether groups exclude groups known to attack borates, such as some acids, and acid halides. Exemplary selected substituents for R$_1$, R$_2$, R$_3$, R$_4$, R$_5$, R$_6$ and/or R$_7$ include halo, esters, alkoxy, hydroxy, alkoxycarbonyl, alkoxyalkyl, alkoxyaryl, borata, and phenyl groups. In general, smaller groups containing 1 to 5 carbon atoms together with one or more than one N, O, or S atoms are preferred for the R$_1$ and R$_2$ groups. By independently selected it is meant that the substituent groups may be the same or that they may be different. Preferably R$_1$ and R$_2$ are identical. R$_1$ and R$_2$ can be part of an internal ring with the boron atom. The ring formed with B, R$_1$ and R$_2$can contain a heteroatom such as O or S. R$_1$ and R$_2$ are preferably ethyl, propyl, or butyl groups.

Alkylene structures represented by —(CR$_3$R$_4$)$_n$— in (I) and (II) include but are not limited to —CH$_2$—, —CH(CH$_3$)—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$C(CH$_3$)$_2$—, —CH$_2$,CH$_2$CH$_2$C(CH$_3$)$_2$—, —C$_6$H$_4$CH$_2$—, —CH$_2$CH(CH$_3$)CH$_2$CH(CH$_3$)CH$_2$—, and the like as can be seen in the following illustrated embodiments where M is a counter ion having positive charge m.

An exemplary reaction scheme in the synthesis of internally blocked alkoxy borate (where X=O) is:

Example 1

Sodium Diethyl(1-Propanolato(2-)—C³,O)Borate

The entire reaction is performed under a dry, inert atmosphere, with care taken to assure that oxygen and water are not allowed to contaminate the reaction or reagents. The reaction is conducted under an argon atmosphere in a jacketed vessel equipped with a stir bar, condenser with argon connection, septum port, and thermometer.

Triethylborane (0.3 mol) in THF was charged to a 500 ml glass reactor and heated to 60–65° C. Pivalic acid (0.005 mol) in toluene was added to the reactor and allowed to react for 15 minutes. Neat 3-bromo-1-propanol (0.3 mol) was added slowly and the reaction allowed to stir at 65–75° C. under reflux for 90 minutes. The reaction was cooled to 30–35° C. and a 30% sodium metal dispersion (0.65 mol) in toluene was added slowly while maintaining the reactor contents below 50° C. The reaction was heated to reflux and allowed to stir for 60 minutes, followed by cooling to around 40° C. and the product mixture added to 5.5 moles of water with moderate stirring, resulting in two phases. The isolated top organic phase was stripped under vacuum at 60° C. The filtered product was obtained in high yield and purity as a yellow oil containing 20–40% residual water. $^1$H (proton) NMR ($D_2O$) δ 3.35, 1.37, 0.58 and −0.03 ppm.

The syntheses of other exemplary internally blocked alkoxy borates are summarized in the following tables.

TABLE 1

| Reactants/Step | Example |
| --- | --- |
| 1. Triethylborane + pivalic acid<br>2. 3-bomopropanol<br>3. sodium | Na⁺ ... Example 1 |
| 1. triethylborane + pivalic acid<br>2. 4-bromobutanol<br>3. sodium | Na⁺ ... Example 2 |
| 1. triethylborane + pivalic acid<br>2. 3-bromo-2-methylpropanol<br>3. sodium | Na⁺ ... Example 3 |
| 1. triethylborane + pivalic acid<br>2. 5-bromopentanol<br>3. sodium | Na⁺ ... Example 4 |
| 1. triethylborane + pivalic acid<br>2. 2-bromomethylphenol<br>3. sodium | Na⁺ ... Example 5 |

Examples 1–7 are illustrated by:

(1)

(2)

(3)

-continued (4)

(5)

(6)

(7)

Internally blocked borates in which X is $CH_2$ can be made by more than one route. The reaction of diborane with 2,4-dimethyl-1,4-pentadiene, followed by reaction with ethylene, and then ethyl sodium results in Example 6 in Table 2. The intermediate cyclic hydroborane is known. This intermediate can be used in accordance with the invention for synthesizing a variety of bi-cyclic borates, for example, by reaction with an olefin and ethyl sodium as can be seen in Examples 11–15 below. The reaction of triethylborane with borane dimethylsulfide is known and results in the formation of diethylborane. Diethylborane can be reacted with 4-bromo-1-butene and then sodium to produce the internally blocked structure of Example 7.

An internally blocked thioborate is formed by reacting triethylborane with borane dimethylsulfide followed by reacting with 4-bromo-1-butene, and then with thiourea, followed by sodium hydroxide, resulting in the internally blocked borate in which X is S, as in example 8.

TABLE 2

| Reactants/step | Example |
| --- | --- |
| 1. diborane + 2,4-dimethyl-1,4-pentadiene<br>2. ethylene<br>3. ethyl sodium | Example 6 |

TABLE 2-continued

| Reactants/step | Example |
| --- | --- |
| 1. triethylborane + borane-dimethylsulfide<br>2. 4-bromo-1-butene<br>3. sodium | Example 7 |
| 1. triethylborane + borane-dimethylsulfide<br>2. 4-bromo-1-butene<br>3. thiourea<br>4. sodium hydroxide | Example 8 |
| 1. diborane + 6 allyl acetate<br>2. sodium ethoxide/ethanol | Example 9 |

Example 9

Sodium di(3-Hydroxypropyl)(1-Propanolato(2-)—$C^3$,O)Borate

A 250-mL round-bottom flask was fit with a stir bar and sealed with a septum. The flask was purged with nitrogen for 30 min and placed in a solid carbon dioxide-isopropanol bath. Borane (150 mL of a 1 M solution in THF, 150 mmol) was added to the reaction flask via syringe. Allyl acetate (49.5 g, 495 mmol), which had been sparged with nitrogen, was added to the reaction flask via syringe. The reaction was allowed to slowly come to room temperature overnight. The reaction was stirred at room temperature for 4 days. The solvent was removed under vacuum. The reaction flask was taken into an argon box. A solution of 4.08 g (170 mmol) of sodium hydride in 40 mL of ethanol (thus, a solution of sodium ethoxide in ethanol) was added to the reaction flask. A white precipitate formed. The reaction flask was fitted with a distillation head and a receiving flask. The apparatus was removed from the argon box and the reaction was heated with slow distillation of the solvent. Freshly distilled ethanol was added as needed. The distillation continued until the distillate no longer contained ethyl acetate (checked by proton NMR). Some insoluble material was separated by filtration and the solvent was removed from the filtrate at 0.4 torr and 80° C. The proton NMR of both the insoluble fraction and the soluble fraction were taken in THF-$d_8$. Both were consistent with the desired product.

This synthesis of Example 9 is summarized as:

TABLE 3

1. 9-BBN
2. 4-bromobutene
3. 2 Na°

Example 10

1. diborane + 2,4-dimethyl-1,4-pentadiene
2. 4-bromo-1-butene
3. 2 Na°

Example 11

1. diborane + 2,4-dimethyl-1,4-pentadiene

Example 12

2.

3. EtO⁻Na⁺/EtOH 1. diborane + 2,4-dimethyl-1,4-pentadiene

Example 13

TABLE 3-continued

2.

3. 2 Na⁺

1. diborane + 2,4-dimethyl-1,4-pentadiene

Example 14

2.

3. EtO⁻Na⁺/EtOH 1. diborane + 2,4-dimethyl-1,4-pentadiene

Example 15

2.

3. EtO⁻Na⁺/EtOH

1) $B_2H_6 + H_2C=CH-CH(CH_2OCOCH_3)-CH=CH_2$
2) NaOEt/EtOH

Example 16

1. $B_2H_6$ + 3

Example 17

2. 2 Et Na

In Example 16, the starting diene alcohol in step 1 is known. The alcohol is converted first to an ester by well known conversion methods. The diene ester derivative is then reacted with diborane followed by reaction with sodium ethoxide/ethanol to provide conversion to the bis borata compound.

The counterion M can be any Group IA (e.g., Li⁺, Na⁺, or K⁺), Group IIA metal, ammonium, tetraalkylammonium, phosphonium, or metal complex with a charge of from +1 to +7, preferably +1, +2, or +3. The preferred counterions are Na⁺, K⁺ and Li⁺. The counterion can be ion exchanged after formation of the internally blocked organoborate.

In the use of any of the internally blocked organoborate as an initiator in a polymerizable adhesive, an effective amount of the blocked organoborate is an amount that is enough to permit polymerization to readily occur after contact with the deblocking agent to obtain adhesive bonding from the polymerizable component for the desired end-use. If the amount of internally blocked organoborate is too high, then the polymerization of the adhesive may proceed too rapidly to allow for effective mixing and application of the polymerizable adhesive to the substrate(s). The useful rate of adhesive polymerization will depend in part on the method of applying the adhesive to the substrate. Thus, the rate of polymerization for a high speed automated industrial applicator can be faster than if the composition is applied with a hand applicator or if the composition is mixed manually.

Generally an adhesive formulation will contain effective amounts of internally blocked organoborate, such as from about 0.1 mol % to about 10 mol % based on the moles of free radical polymerizable component(s). This range provides useful results. Good adhesive bond strength was obtained using acrylic polymerizable components with from 1.5 to 6 mol % of internally blocked organoborate initiator.

Suitable deblocking agents that liberate the active organoborane initiator include acids. Useful acids that de-block the organoborate include Lewis acids (e.g., $SnCl_4$, $TiCl_4$, and the like) and Brønsted acids such as those monofunctional acids having the general formula R'—COOH, $R'SO_3H$, where R' is hydrogen, an alkyl group, or an alkenyl group of 1 to 12 and preferably 1 to 6 carbon atoms, or an aryl group of 6 to 10 carbon atoms. Carboxylates having more than one acidic moiety can be used. The alkyl and alkenyl groups on a monofunctional carboxylic acid used as a deblocking agent may comprise a straight chain or they may be branched. Such groups may be saturated or unsaturated. The aryl groups may contain substituents such as alkyl, alkoxy or halogen moieties. Adducts of an anhydride and hydroxy-functional monomers are especially useful deblocking agents, for example an adduct of maleic anhydride and hydroxyethyl methacrylate (MA-HEMA adduct). Specific examples as illustrative acids include acrylic acid, dimerized or oligomerized acrylic acid, methacrylic acid, acetic acid, benzoic acid, methanesulfonic acid, and p-methoxybenzoic acid. Other useful Bronsted acids include HCl, $H_2SO_4$, $H_3PO_4$ and the like. $SnCl_4$, acrylic acid, methacrylic acid and an MA-HEMA adduct are preferred acid deblocking agents.

Non-acid deblocking agents which are known may be used, such as those disclosed in U.S. Pat. Nos. 5,286,821; 5,376,746; 5,621,143; 5,684,102 incorporated herein by reference. Example deblocking agents include acylating agents, alkylating agents, aldehydes and sulfonic acid chlorides, to name a few of the known deblocking agents. Examples of acylating agents include acid chlorides, anhydrides, isocyanates and carbodiimides. Alkylating agents include, β-haloamines, β-halosulfides (mustards), benzyl bromide, and allyl bromide. The alkylating agent methoxyethoxymethyl chloride has been shown to be effective for activating the blocked borate of example 1.

The deblocking agent should be used in an amount effective to promote polymerization. If too little agent is employed, the rate of polymerization may be too slow. However, a reduced amount of acid may be helpful in slowing the rate of polymerization. If too much acid is used, then the polymerization tends to proceed too quickly and, in the case of adhesives, tends to decrease open time. Within these parameters, the acid should, preferably, be provided in an adhesive in an amount of about 30 to 540 mole % based on the number of equivalents of internally blocked initiator functionality, more preferably about 80 to 350 mol %, and most preferably about 100 to 200 mol % based on the equivalents of initiator functionality of the borate.

Adhesives can contain optionally a non-borane free radical initiator which are well known in the art. A non-borane free radical initiator can readily be contained in the polymerizable monomer part of a two-part polymerizable composition. Preferred non-borane free radical initiators are those which do not readily react with monomer under shelf-aging conditions, or can be inhibited suitably to provide desired shelf stability of up to several months, if needed. Illustrative examples of suitable non-borane free radical initiators optionally employed in combination with the polymerizable monomers described above include organic hydroperoxy initiators, particularly those organic peroxides and hydroperoxides having the formula R"OOR" and R"OOH, respectively, wherein R" is a hydrocarbon radical containing up to about 18 carbon atoms, preferably an alkyl, aryl, or aryl alkyl radical containing from one to 12 carbon atoms. Specific examples of such hydroperoxides are cumene hydroperoxide, tertiary-butyl hydroperoxide, methyl ethyl ketone peroxide, and hydroperoxides formed by the oxygenation of various hydrocarbons, such as methylbutene, cetane, and cyclohexene, and various ketones and ethers. Other examples of useful initiators include hydroperoxides such as p-menthane hydroperoxide, 2,5-dimethylhexane, 2,5-dihydroperoxide and the like. Additionally, more than one non-borane free radical initiator may be employed, such as a mixture of hydroperoxides with peresters, such as t-butyl perbenzoate or t-butylperoxymaleate, can be advantageously used. For reasons of economics, availability, and stability, cumene hydroperoxide is especially preferred.

The invention is adapted to a variety of addition polymerizable compositions which are also referred to as curable compositions, such as described in U.S. Pat. Nos. 2,981,650; 3,321,351; 4,223,115; 4,293,665; 4,467,071; 4,452,944; and 4,769,419, the entire disclosure of each of which is hereby incorporated by reference. The addition polymerizable compositions of the invention polymerize in the presence of internally blocked organoborate when the blocking group is de-coupled from boron by the de-blocking agent. Addition polymerizable compounds include free radical polymerizable compounds such as olefinic monomers which are characterized by the presence of a >C=C< group. Exemplary preferred olefinically unsaturated monomers include substituted and unsubstituted acrylic acid, and their amides, esters, salts and corresponding nitrites, as well as substituted and unsubstituted styrene, and the like. Representative free radical-polymerizable monomers include, but are not limited to, styrene, vinyl styrene, vinyl acetate, chlorostyrene, vinylidene chloride, 2,3-dichloro-1,3-butadiene, 2-chloro-1, 3-butadiene, methylstyrene, p-tert-butyl styrene, esters of fumaric and maleic acid which are capable of free radical polymerization, and mixtures thereof. The polymerizable compositions of the invention typically include at least one free radical polymerizable compound in an amount from about 10 to about 99, preferably about 20 to about 75 weight percent based on the total weight of the polymerizable composition.

The preferred free radical polymerizable compounds are α,β-unsaturated esters, such as acrylic and methacrylic moieties or chemical groups; that is, groups which have the general structure III:

(III)

wherein R is H or an organic radical, and R and R' are substituted and unsubstituted organic radicals that may be the same or different.

The polymerizable components can be monofunctional and/or polyfunctional including a combination of monofunctional and polyfunctional monomers, oligomers and polymers, including mixtures thereof. There are widely available monofunctional acrylate and methacrylate esters, and the substituted versions such as hydroxy, amide, cyano, chloro, and silane substituted derivatives. Specific examples include methyl acrylate, methyl methacrylate, ethyl acrylate, ethyl methacrylate, butyl methacrylate, butyl acrylate, cyclohexyl acrylate, hexyl acrylate, 2-ethylhexyl acrylate, isobornyl methacrylate, hydroxyethyl methacrylate, hydroxypropyl acrylate, hydroxypropyl methacrylate, n-octyl acrylate, cyclohexyl methacrylate, hexyl methacrylate, 2-ethylhexyl methacrylate, decyl methacrylate, dodecyl methacrylate, lauryl acrylate, tert-butyl methacrylate, acrylamide, N-methyl acrylamide, diacetone acrylamide, N-tert-butyl acrylamide, N-tert-octyl acrylamide, N-butoxyacrylamide, gamma-methacryloxypropyl trimethoxysilane, dicyclopentadienyloxyethyl methacrylate, 2-cyanoethyl acrylate, 3-cyanopropyl acrylate, tetrahydrofurfuryl methacrylate, tetrahydrofurfuryl acrylate, glycidyl acrylate, acrylic acid, methacrylic acid, itaconic acid, glycidyl methacrylate. Basic monomers such as dimethylaminoethyl acrylate and dimethylamino methacrylate could be employed provided that sufficient amounts of acidic deblocking agents are used.

Particularly preferred polymerizable components are mixtures of $C_1$–$C_4$ alkyl acrylates (e.g., methyl, ethyl, propyl, and butyl acrylate) and $C_1$–$C_4$-alkyl methacrylates (e.g., methyl methacrylate, ethyl methacrylate, and the like), tetrahydrofurfuryl methacrylate and tetrahydrofurfuryl acrylate, including mixtures of the preferred polymerizable components. The polymerizable compositions according to the invention may broadly comprise, based on the total weight of the composition, about 10 to 80 wt. % (more preferably about 30 to 70 wt. %) of the alkyl methacrylate, and about 0 to 50 wt. % (more preferably about 2 to 20 wt. %) of the alkyl acrylate.

Another useful class of polymerizable monomers corresponds to the general formula IV:

IV wherein for structure IV, $R_8$ may be selected from the group consisting of hydrogen, methyl, ethyl, —$CH_2OH$, and

$R_9$ may be selected from the group consisting of chlorine, methyl and ethyl. $R_{10}$ may be selected from the group consisting of hydrogen, hydroxy, and The value of "a" in IV is an integer greater than or equal to 1, preferably "a" represents 1 to 8 —$CH_2$— groups. The integral value of "b" is greater than or equal to 1, preferably 1 to 20, and "c" is 0 or 1.

The optional multifunctional monomers provide crosslinking. A suggested amount of crosslinking monomer, if used, is 0.1 to 20 weight percent, and preferably 0.5 to 10 weight percent, based on the weight of the composition, and can be predetermined depending on the physical properties of the cured material as is known and practiced in the art. Useful crosslinkers include glycol- and polyether diacrylates and dimethacrylates, such as, ethylene glycol dimethacrylate, ethylene glycol diacrylate, diethylene glycol dimethacrylate, triethyleneglycol dimethacrylate, diethylene glycol bismethacryloxy carbonate, tetraethylene glycol dimethacrylate, diglycerol diacrylate, pentaerythritol triacrylate, trimethylopropane trimethacrylate, polyethylene glycol diacrylate, dimethacrylate of bis(ethylene glycol) adipate, dimethacrylate of bis(ethylene glycol)maleate, dimethacrylate of bis(ethylene glycol)phthalate, dimethacrylate of bis(tetraethylene glycol)phthalate, dimethacrylate of bis(tetraethylene glycol)sebacate, dimethacrylates of bis(tetraethylene glycol)maleate, and the like.

Also useful are monomers that are the known and widely available isocyanate-hydroxyacrylate or isocyanate-aminoacrylate reaction products. These may be characterized as acrylate terminated polyurethanes (also referred to as acrylourethane) and polyureides or polyureas. Such monomers have the following general formula:

where X is selected from the group consisting of —O— and >N-$R^{10}$, where $R^{10}$ is selected from the group consisting of hydrogen and lower alkyl groups (i.e., 1 to 7 carbon atoms). T is the organic residue of an active hydrogen-containing acrylic ester the active hydrogen having been removed and the ester being hydroxy or amino substituted on the alkyl portion thereof (including the methyl, ethyl and chlorine homologues). The integral value of "d" is from 1 to 6. L is a mono- or polyvalent organic radical selected from the group consisting of alkyl, alkylene, alkenyl, cycloalkyl, cycloalkylene, aryl, aralkyl, alkaryl, poly(oxyalkylene), poly(carboalkoxyalkylene), and heterocyclic radicals, both substituted and unsubstituted. Typical monomers of this class include the reaction product of mono- or polyisocyanates, for example, toluene diisocyanate, with an acrylate ester containing a hydroxy or an amino group in the non-acrylate portion thereof, for example, hydroxyethyl methacrylate.

Another class of monomers useful herein are the mono- and polyacrylate and methacrylate esters of bisphenol-type compounds many of which are widely available. Representative monomers of the bisphenol type include dimethacrylate and diacrylate esters of 4,4'-bis-hydroxyethoxybisphenol A, dimethacrylate and diacrylate esters of bisphenol A, etc.

Epoxy compounds can be included in the adhesive compositions of the invention in amounts from 0 to about 40, preferably 0 to about 20, weight % based on the total weight of the composition. The addition of an epoxy compound can impart heat resistance to the compositions. Epoxy compounds that are suitable for use in the invention are described in U.S. Pat. No. 4,467,071, referenced above, and can be any monomeric or polymeric compound or mixture of compounds having an average of greater than one 1,2-epoxy groups per molecule. The polymeric epoxide compounds can have a number average molecular weight from about 300 to about 10,000. Epoxy compounds are well-known, and disclosed in U.S. Pat. Nos. 2,467,171; 2,615,007; 2,716,123; 3,030,336 and 3,053,855. Useful epoxy compounds include the polyglycidyl ethers of polyhydric alcohols, such as ethylene glycol, triethylene glycol, 1,2-propylene glycol, 1,5-pentanediol, 1,2,6-hexanetriol, glycerol and 2,2-bis(4-hydroxy-cyclohexyl)propane; the polyglycidyl esters of aliphatic or aromatic polycarboxylic acids, such as oxalic acid, succinic acid, glutaric acid, terephthalic acid, 2,6-naphthalene dicarboxylic acid and dimerized linolenic acid; and the polyglycidyl ethers of polyphenols, such as bisphenol A, 1,1-bis(4-hydroxyphenyl)ethane, 1,1-bis (hydroxyphenyl)isobutane, 2,2-bis (4-hydroxy-t-butylphenyl)propane, 1,5-dihydroxynaphthalene and novolak resins.

The compositions of the invention advantageously also include at least one optional polymeric material which can provide toughness, impact and shatter resistance to the resultant adhesive and to decrease the brittleness thereof. The polymeric material may or may not include an olefinically unsaturated structure that is capable of being polymerized per se or copolymerized with at least one of the free radical polymerizable monomers described above. The polymeric material can be, for example, polychloroprene as described in U.S. Pat. No. 2,981,650, referenced above; a polymer-in-monomer syrup as described in U.S. Pat. Nos. 2,981,650; 3,321,351; and 4,223,115; various solid and liquid elastomeric polymeric materials like amine, or carboxy terminated butadiene-acrylonitrile, ie., ATBN, and CTBN, and in particular liquid olefinic-terminated elastomers (e.g., olefin terminated polyalkadiene, butadiene-based elastomers and urethane-modified butadiene-based elastomers as described in U.S. Pat. Nos. 4,223,115; 4,452,944; and 4,769,419, and 5,641,834; chlorosulfonated polyethylene rubbers, as described, for example, in U.S. Pat. No. 4,223,115; olefinic urethane reaction products of an isocyanate-functional prepolymer and a hydroxy-functional monomer, as described in U.S. Pat. Nos. 4,223,115; 4,452,944; 4,467,071; and 4,769,419, referenced above; and triblock copolymers of the general configuration A-B-A, wherein A is an alkenyl aromatic hydrocarbon polymer block and B is a conjugated diene hydrocarbon polymer block. Alkenyl aromatic hydrocarbons are useful as the A blocks and the B portion can be any four to ten carbon conjugated diene. Specific examples of A-B-A block copolymers include polystyrene-polyisoprene-polystyrene, poly(α-methylstyrene)-polyisoprene-poly(o-methylstyrene) and polystyrene-polybutadiene-polystyrene.

Polymer-in-monomer syrups, compositionally as well as their preparation, are well known in the art. Representative syrups including precursor liquid monomer compounds containing at least one olefinically unsaturated group, and their preparations are disclosed in U.S. Pat. Nos. 3,333,025; 3,725,504; and 3,873,640, the entire disclosure of each of which is hereby incorporated by reference.

Representative liquid olefinic-terminated elastomers include homopolymers of butadiene; copolymers of butadiene and at least one monomer copolymerizable therewith, for example, styrene, acrylonitrile, methacrylonitrile (e.g., poly(butadiene-(meth)acrylonitrile) or poly(butadiene-(meth)acrylonitrile-styrene) and mixtures thereof; as well as modified elastomeric polymeric materials, such as butadiene homopolymers and copolymers as noted above modified by copolymerization therewith of trace amounts of up to about 5 percent by weight of the elastomeric material of at least one functional monomer (such as acrylic acid, methacrylic acid, maleic anhydride, fumaric acid, styrene, and methyl methacrylate, to give, for example, methacrylate-terminated polybutadiene homopolymers and/or copolymers of butadiene).

As described in U.S. Pat. No. 4,769,419, referenced above, the second hydroxyl group of liquid butadiene-based elastomers can be reacted with an isocyanate to form a liquid urethane-modified butadiene elastomer.

Representative urethane-modified butadiene-based elastomeric polymeric compounds and processing for preparing the same are described in U.S. Pat. No. 4,769,419.

Such liquid olefinic-terminated elastomers can be present in the compositions of the invention in amounts from about 10 to about 80, preferably about 20 to about 50, weight percent based on the total weight of the composition.

Exemplary chlorosulfonated polyethylene rubbers are described in U.S. Pat. No. 4,223,115 and include chlorosulfonated polyethylene and a mixture of sulfonyl chloride with chlorinated polyethylene. These compositions can have a chlorine content in the range of about 25 to about 67 weight percent and from 3 to about 160 mmols sulfonyl chloride moiety per 100 grams of polymer. Further, the polyethylene from which the chlorosulfonated polyethylene is made preferably has a melt index in the range from about 4 to about 500.

Representative olefinic urethane reaction products of isocyanate-functional prepolymers and hydroxy-functional monomers having at least one unit of polymerizable unsaturation characterized by the presence of at least two units of unsaturation and the substantial absence of free isocyanate groups are also well-known. Typically, such prepolymers are adducts or condensation products of polyisocyanate compounds having at least two free isocyanate groups and monomeric or polymeric polyols having at least two hydroxy groups, including mixtures of such polyols. The reaction between the polyisocyanate and the polyols is effected employing an excess amount of polyisocyanate to ensure that the reaction product will contain at least two free, unreacted isocyanate groups. Such olefinic urethane reaction products can be present in the compositions of the invention in amounts from 0 to about 40, preferably about 1 to about 25, weight percent based on the total weight of the composition.

Advantageously, the adhesive compositions of the present invention optionally include a phosphorus-containing compound having one or more olefinic groups and no fewer than one P—OH group. Phosphorus-containing compounds, which have been found to enhance metal adhesion, are selected from the group consisting of derivatives of phosphinic acid, phosphonic acid and phosphoric acid having at least one P—OH group and at least one organic moiety characterized by the presence of an olefinic group, which is preferably terminally located. A listing of such phosphorus-containing compounds is found in U.S. Pat. No. 4,223,115, referenced above. Such phosphorus-containing compounds can be utilized in amounts of from about 0.1 to about 20, preferably about 2 to about 10, percent by weight, based on the total weight of the composition.

A preferred phosphorus-containing compound has a structure that may be represented by the formula V wherein $R_{11}$ is selected from the group consisting of hydrogen, an alkyl group having from 1 to 8, preferably 1 to 4, carbon atoms, and $CH_2=CH-$; $R_{12}$ is selected from the group consisting of hydrogen, an alkyl group having from one to 8, preferably one to 4 carbon atoms; A is selected from the group consisting of $-R_{13}O-$ and $(R_{14}O)_n$, wherein $R_{13}$ is an aliphatic or cycloaliphatic alkylene group containing from one to 9, preferably 2 to 6, carbon atoms; $R_{14}$ is an alkylene group having from one to 7, preferably 2 to 4, carbon atoms; n is an integer from 2 to 10, and m is 1 or 2, and preferably m=1.

Monoesters of phosphinic, phosphonic and phosphoric acids having one unit of vinyl or allylic, especially vinyl unsaturation are preferred optional adhesion promoting compounds includable herein. Representative phosphorus-containing compounds include, without limitation, 2-methacryloyloxyethyl phosphate; bis-(2-methacryloxyloxyethyl) phosphate; 2-acryloyloxyethyl phosphate; bis-(2-acryloyloxyethyl) phosphate; methyl-(2-methacryloyloxyethyl) phosphate; ethyl methacryloyloxyethyl phosphate; methyl acryloyloxyethyl phosphate; ethyl acryloyloxyethyl phosphate; compounds of the above formula wherein $R^{12}$ is hydrogen or methyl and $R^{11}$ is propyl, isobutyl, ethylhexyl, halopropyl, haloisobutyl or haloethylhexyl; vinyl phosphonic acid; cyclohexene-3-phosphonic acid; alphahydroxybutene-2 phosphonic acid; 1-hydroxy-1-phenylmethane-1,1-diphosphonic acid; 1-hydroxy-1-methyl-1-disphosphonic acid: 1-amino-1 phenyl-1,1-diphosphonic acid; 3-amino-1-hydroxypropane-1,1-disphosphonic acid; amino-tris (methylenephosphonic acid); gamma-amino-propylphosphonic acid; gamma-glycidoxypropylphosphonic acid; phosphoric acid-mono-2-aminoethyl ester; allyl phosphonic acid; allyl phosphinic acid; .beta.-methacryloyloxyethyl phosphinic acid; diallylphosphinic acid; β-methacryloyloxyethyl) phosphinic acid and allyl methacryloyloxyethyl phosphinic acid.

The compositions of the invention can also optionally contain from zero to about 10 percent by weight based on the total weight of the composition of at least one unsaturated polyester resin. Unsaturated polyester resins suitable for use in the adhesive systems described herein are well known in the art. Such resin esters are derived from polycarboxylic acids and polyhydric alcohols, preferably dicarboxylic acids and dihydric alcohols, at least one of the acid and alcohol components being unsaturated. Preferably, the unsaturated polyester resin component will contain a relatively large number of double bonds and be derived from short chain aliphatic polyhydric polyols, such as ethylene glycol and 1,3-propylene glycol, and short chain unsaturated polybasic acids, such as fumaric acid and maleic acid. Such resins can contain quantities of longer chain polyols such as 1,6-hexanediol, as well as higher polybasic acids, such as adipic acid and phthalic acid.

Still further, the compositions of the invention can optionally contain from zero to about 50 percent by weight based on the total weight of the adhesive composition of at least one polyvinyl alkyl ether. Polyvinyl alkyl ethers are well-known in the art. Such ethers will preferably contain 1–8, more preferably 1–4, carbon atoms in the alkyl moiety of the ether. Likewise, styrene-acrylonitrile polymers which are suitable for use in the invention are also well known.

The compositions of the invention can also include up to about 60, preferably not more than about 30, percent by weight based on the total weight of the composition of a pre-formed polymeric component. Exemplary preferred polymeric materials include poly(methyl methacrylate), polystyrene, poly(methyl methacrylate/n-butylacrylate/ethyl acrylate) (90/5/5); poly (n-butyl methacrylate/isobutyl methacrylate) (50/50); poly(n-butyl methacrylate), poly (ethyl methacrylate), and poly(tetrahydrofurfuryl methacrylate).

The compositions may further comprise a variety of optional additives. One particularly useful additive is a low (i.e., less than or equal to about 100,000) molecular weight poly(methyl methacrylate) which may be incorporated in an amount of about 20 to 40 wt. % (weight percent), based on the weight of the composition. Other thickeners such as fumed silica may be employed to increase the viscosity of the composition to a more easily applied viscous syrup- or paste-like consistency.

Various known plasticizers may be added to improve flexibility and/or toughness. Other useful conventional additives optionally included are non-reactive pigments, colorants, fillers (e.g., carbon black), etc. The optional additives are employed in an amount that does not significantly adversely affect the polymerization process or the desired properties of compositions made therewith.

The substrate which can be bonded together, or to other substrate(s) in accordance with the present invention may be any substrate known to those of skill in the art. For example, the substrate may be, but is not limited to, woven or nonwoven fabrics, fibers, such as fiberglass, polyamides, polyester, aramids, e.g., Kevlar®, a trademark of E. I. du Pont de Nemours Co., (Inc.), of Wilmington, Del., glass, ceramics, metals, and especially thermoplastic and thermoset polymers, and the like. Metals and their alloys include, but are not limited to, steel, stainless steel, lead, aluminum, copper, brass, bronze, Monel metals, nickel, zinc, and the like, including treated metals such as phosphatized steel, galvanized steel, and the like.

The invention is particularly useful for adhesively bonding together low surface energy substrates or in crossbonding a low energy substrate with different substrates. A low surface energy substrate is defined as one having a surface energy of less than 45 mJ/m$^2$, preferably less than 40 mJ/m$^2$ or even less than 35 mJ/m$^2$. Included among the recognized low surface energy substrates are materials such as polyethylene, polypropylene, copolymers of a-olefins, acrylonitrile-butadiene-styrene, polyamide, and fluorinated polymers such as polytetrafluoroethylene. Other polymers of somewhat higher surface energy that can be structurally bonded with the adhesive compositions of the invention include polycarbonate and poly(methyl methacrylate). However, the invention is not so limited to bonding of low surface energy materials, but is a distinctive feature. The compositions may be used to bond any thermoplastic as well as wood, ceramics, glass, concrete and non-primed and primed metals together or especially in bonding different substrates, i.e., crossbonding one substrate to a different substrate.

The polymerizable compositions of the invention are effective as contained and dispensed from two-part dispensers. A one-part embodiment can be made but is not preferred. The components of the polymerizable composition are blended as would normally be done when working with such materials. An optional accelerator component of the polymerization initiator system can be included in this blend so as to separate it from the internally blocked organoborate, thus providing one part of the two-part composition. The internally blocked organoborate of the polymerization initiator system provides the second part of the composition in a carrier.

The internally blocked organoborate may advantageously be contained in one part as a mixture in a carrier. The carrier may be a liquid having low volatility that can be mixed directly, or those having film-forming properties by themselves. Any suitable carrier can be chosen depending on the application techniques desired, and can be a simple inert solvent or diluent such as methylene chloride, or butyl benzyl phthalate, including mixtures of such solvents or diluents. The carrier can be a liquid polymer in addition to an inert solvent or diluent. The carrier is preferably substantially inert with respect to the borate when present in the composition. A carrier vehicle may contain one or more film-formers. Among the polymeric film-former materials which can be employed in the carrier vehicle are, without limitation, polyalkylacrylates and methacrylates and copolymers thereof, polystyrene and copolymers thereof, vinyl polymers and copolymers, polyesters, polyketones, polysulfones, phenolic resins, polyvinyl acetals and butyrals, and polycarbonates. The carrier vehicle can contain, in addition to solvent or solvent and film-former, additives such as external plasticizers, flexibilizers, suspenders, and stabilizers, providing that any such additives do not unacceptably adversely affect the stability of the borate composition. Specific examples of preferred liquid polymers are polyester adipates, polypropylene glycol and Kraton® liquid polymers.

Specific examples of carriers are plasticizers such as aliphatic and aromatic esters of phthalic acid, aliphatic and aromatic esters of phosphoric acid, aliphatic trimellitate esters, aliphatic esters of adipic acid, as well as stearate, sebacate and oleate esters. Process oils commonly used in the elastomer industry such as aromatic process oil, paraffinic process oil, and napthenic process oil can be used. Liquid polymers such as low molecular weight polyester, low molecular weight polyisobutylene, or silicone oil are suitable. Hydrogenated polybutadiene and polyisoprene polymers may also be useful as carriers.

In a two-part adhesive embodiment, the parts can be mixed as they are dispensed or shortly before it is desired to use the composition. The internally blocked organoborate compound may be added to the first part predissolved in carrier solvent or dispersed in a non-solvent carrier. Once the two parts have been combined, the composition should be used quickly. The useful pot life may be on the order of several minutes depending upon the specific internally blocked organoborate, amount thereof, the polymerizable components, the presence and amount of accelerator, and the temperature of the parts as applied.

In an adhesive, the mixed initiator/polymerizable composition is applied to one or both substrates and then the substrates are joined together with pressure to force excess composition out of the bond line. In general, the bonds should be made shortly after the composition has been applied, preferably within about 10 minutes. The typical bond line thickness is generally within 25 $\mu$m to 500 $\mu$m thick. The bonding process can easily be carried out at room temperature and to improve the degree of polymerization it is desirable to keep the temperature at or above room temperature.

The bonds will cure to a reasonable green strength to permit handling of the bonded components within about 2 to 3 hours. Full strength will be reached in about 24 hours under ambient conditions; post-curing with heat may be used if desired.

Bonding Examples

The general method used in the lap shear bonding examples is given below. The coupons used in this study were 1"×4"×⅛" (2.54×10.16×0.31 cm.) for the plastic coupons and 1"×4"33 ¹⁄₃₂" (2.54×10.16×0.08 cm.) for the metal coupons. The adhesive was dispensed onto one face of each substrate pair. Glass beads (10 mil) were used to maintain a uniform bond-line thickness. The two coupons were mated with a 1 in.$^2$ (6.45 cm.$^2$) bond area and held with a 170 g weight for a cure time of 24 hr. Five to ten coupon pairs constituted each set of lap shear samples. The cured samples were pulled on a mechanical tensile tester at 0.5 in/minute.

Examples 18–25

An acrylic adhesive was prepared using the internally blocked organoborate of Example 1. The components were mixed immediately prior to bonding the coupons and consisted of:

| Component | wt % amount |
|---|---|
| THF Methacrylate | 74.7% |
| Styrene-isoprene-styrene copolymer | 18.7% |
| Methacrylic acid | 3.6% |
| Internally blocked borate from Example 1 | 3.0% |

The adhesive was used to prepare lap shear samples according to the schedule given in the Table below.

| Example | Substrate 1 | Substrate 2 | Mean stress at break | Std. dev. | Failure mode |
|---|---|---|---|---|---|
| 18 | PP | PP | 530 psi | 11 psi | SB |
| 19 | LDPE | LDPE | 151 psi | 15 psi | SN & A |
| 20 | Steel | Steel | 1297 psi | 90 psi | A & C |
| 21 | Steel | PP | 589 psi | 3 psi | PP SN |
| 22 | PTFE | PTFE | 247 psi | 8 psi | SN |
| 23 | Aluminum | Aluminum | 1728 psi | 190 psi | C |
| 24 | Aluminum | PP | 625 psi | 5 psi | PP SB |
| 25 | Aluminum | LDPE | 188 psi | 9 psi | LDPE SN |

PP = polypropylene, LDPE = low-density polyethylene,
PTFE = poly(tetrafluoroethylene); SN = stock necking, SB = stock break,
A = adhesive, C = cohesive.

Example 26

Stability to Air (Oxygen Induced Decomposition)

To demonstrate the air stability of internally blocked organoborate Example 1, a sample of the initiator was exposed to air for 7 days. Using this material, a test adhesive given in Example 18 was prepared. Polypropylene lap shear samples were joined after a predetermined open time (minutes) and cured. Five of the lap shear samples exhibited stock break and one exhibited thin-layer cohesive failure. The mean lap shear strength was 474 psi (3555 Kpa). In contrast, the non-internally blocked alkoxyborate sodium ethoxotriethylborate(III), Na$^+$[B(OCH$_2$CH$_3$)(CH$_2$CH$_3$)$_3$]$^-$, became completely inactive after 24 hours exposure to air.

Example 27

Shelf Stability

The package shelf stability of the internally blocked borate initiated adhesives is shown by evaluating the adhesive's ability to provide good bonding after long term storage in a container capable of storage of separate adhesive component parts with mix-dispensing on application (2-part cartridge) as are employed commercially. The following formulation was prepared and packaged into 2-part cartridges having a volume mixing ratio of 10 parts A: 1 part B:

|  | wt % amount |
|---|---|
| A-side Component |  |
| THF Methacrylate | 53.3% |
| 2-ethylhexyl methacrylate | 16.4% |
| mono-2-(methacryloyloxy)ethyl succinate | 6.0% |
| Core-shell ABS copolymer | 14.5% |
| Glass microspheres | 7.0% |
| Silica | 2.9% |
| B-side Component |  |
| Polypropylene glycol-adipate carrier | 75% |
| Internally blocked borate from Example 1 Na⁺[B(CH₂CH₂CH₂O)(CH₂CH₃)₂]⁻ which is sodium diethyl(1-propanolato(2-)-C³, O)borate (III) | 25% |

Two 2-part cartridges were prepared from the same lots of A- and B-sides. One cartridge was immediately used to bond PP lap shear samples, and the other was allowed to age at ambient lab conditions. After 3 months, the aged cartridge appeared unchanged, and lap shear strengths of bonded PP coupons using the aged cartridge were as good as the results obtained with the unaged cartridge.

Examples 28 and 29

Figure 1:
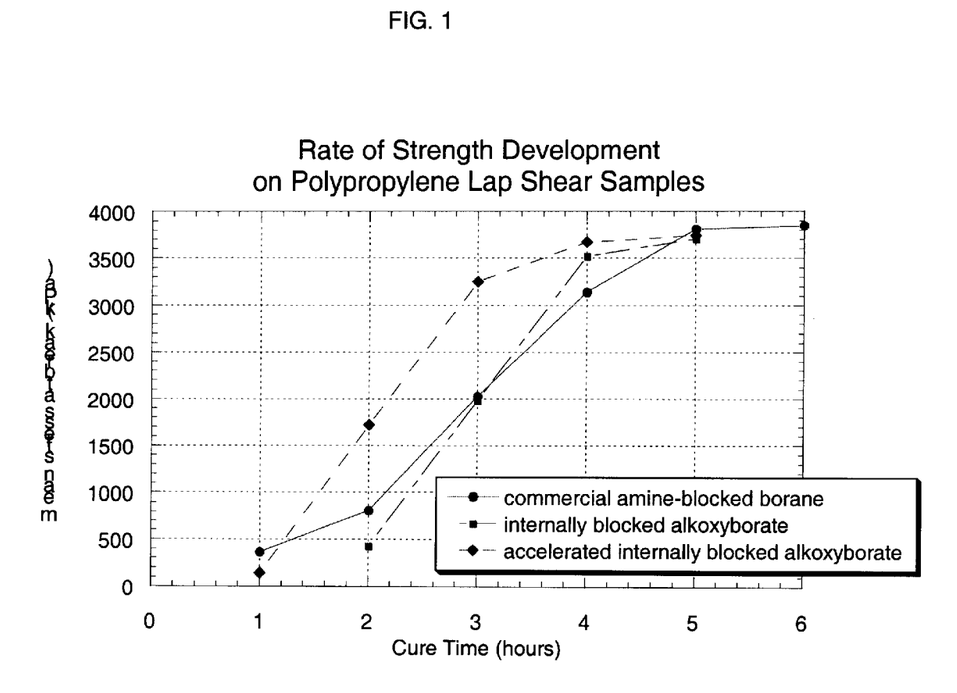
FIG. 1 is an illustration of the rise in adhesive lap shear bond strength for polypropylene as a function of cure time using (a), a commercial amine borane complex, (b) an internally blocked alkoxyborate of the present invention, and (c) an accelerated internally blocked alkoxyborate.

FIG. 1 compares lap shear strength as a function of time obtained in bonding polypropylene coupons together using an adhesive initiated with the internally blocked alkoxy borate (Example 28) and accelerated embodiment (Example 29) against a commercially available borane-amine complex-initiated acrylic adhesive. The formulation for example 28 was the same as that given in example 27. The formulation for example 29 was the same as in example 27 except that 0.01% of the A-side was benzoyl peroxide and 0.1% of the B-side was N,N-dimethylaniline, and example 29 was mixed in a 10:1 volume ratio. The cure rate of the internally blocked alkoxyborate was similar to that of the commercial amine-blocked borane adhesive, though it was slower to develop handling strength (about 100 psi). In contrast, the accelerated formulation shows a much faster rate of strength development.

Example 30

Open Time Study

Figure 2:
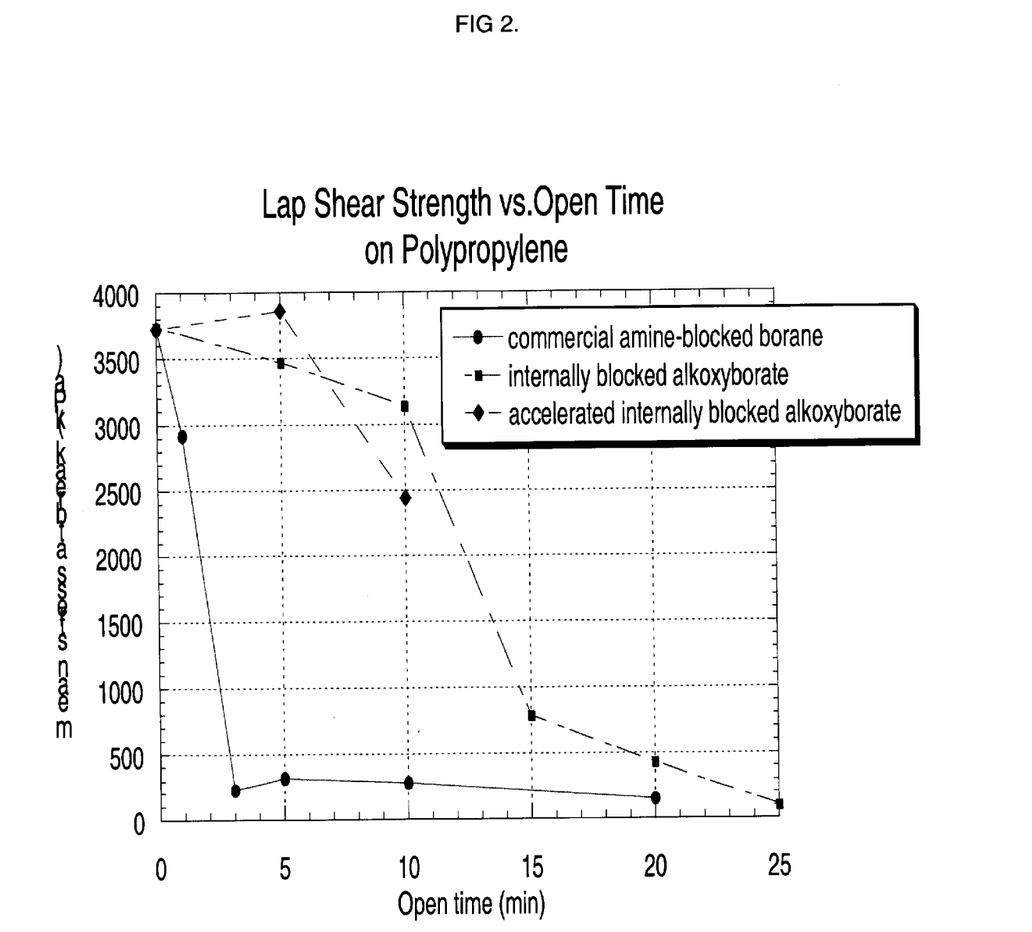
FIG. 2, is an illustration of the adhesive lap shear strength of polypropylene as a function of adhesive open time using (a) a commercial amine borane complex, (b) internally blocked borate, and (c) an accelerated internally blocked borate.

FIG. 2, illustrates that the open time for acrylic adhesive initiated with internally blocked alkoxyborate adhesive is much better than for a commercial amine-blocked borane adhesive. The open time for the amine-blocked organoborane was less than three minutes. The lap shear strength falls from over 500 psi (3750 KPa) to less than 50 psi (375 KPa) if the samples are held open for 3 minutes. In contrast, the adhesive prepared in Example 27 alkoxy borate had an open time of at least five minutes with little drop in lap shear strength, and still good lap shear strength after having delayed bonding for 10 minutes. The BPO/DMA-accelerated system of Example 29 had a shorter open time, but exhibited at least a five-minute open time.

It is understood that the foregoing description of preferred embodiments is illustrative, and that variations may be made in the present invention without departing from the spirit and scope of the invention. Although illustrated embodiments of the invention have been shown and described, a latitude of modification, change and substitution is intended in the foregoing disclosure, and in certain instances some features of the invention will be employed without a corresponding use of other features. Accordingly, it is appropriate that the appended claims are to be construed in a manner consistent with the scope of the invention.

We claim:

1. A method for adhesively bonding substrates, the method comprising the steps of:
    (a) providing at least a first and a second substrate;
    (b) applying a mixture to at least one of said first and said second substrates, said mixture comprising:
        (i) at least one addition polymerizable component;
        (ii) an effective amount of an internally blocked borate compound having a ring structure (II) or (II')

wherein X represents —CHR₇—, oxygen or sulfur; n is the integer 1, 2, 3, 4, or 5, and R₁, R₂, R₃, R₄, R₅, R₆ and R₇ are independently selected from unsubstituted and substituted alkyl or alkylene groups containing 1 to 10 carbon atoms, substituted aryl groups having up to 7 to 12 carbon atoms, and unsubstituted aryl groups; alternatively either of R₃, R₄, R₅, R₆ and R₇ are hydrogen; R₁ and R₂ alternatively are part of a second unsubstituted or substituted cyclic borate; R₁ and R₂ alternatively comprise a spiro ring or a spiro-ether ring; R₁ or R₂ together with R₃ or R₄ alternatively are linked to form a cycloaliphatic ring; and R₁ or R₂ together with either R₃ or R₄ alternatively comprise a cyclic ether ring; and M is any positively charged species with charge m greater than 0 and
        (iii) a deblocking agent;
    (c) mating the first and second substrates with said mixture of step (b) therebetween; and
    (d) allowing the at least one addition polymerizable component to polymerize, optionally with application of heat, whereby the first and second substrates are adhesively bonding.

2. The method according to claim 1 wherein one of said first and said second substrate comprises a material selected from the group consisting of a wood product, thermoplastic material, a thermoset material, and coated or uncoated metal.

3. The method according to claim 2 wherein one of said first and said second substrate comprise materials selected from the group consisting polyethylene, polypropylene, polyurethane, polyurea, fluoroplastic, polyvinylchloride, thermoset polymer, elastomer, aluminum, and steel.

4. The method according to claim 1 wherein said mixture further comprises (iv) an accelerator.

5. The method according to claim 1 wherein the at least one addition polymerizable component comprises a monofunctional methacrylate ester selected from the group consisting of methyl methacrylate, ethyl methacrylate, methoxy ethyl methacrylate, hydroxyethyl methacrylate, hydroxypropyl methacrylate, cyclohexyl methacrylate, tetrahydrofurfuryl methacrylate, and blends thereof.

6. The method according to claim 5 wherein the methacrylate ester monomer is tetrahyrdrofurfuryl methacrylate, and said addition polymerizable component further comprises an alkyl acrylate.

7. The method according to claim 1 wherein said mixture further comprises a thickening agent.

8. The method according to claim 1 wherein said mixture further comprises an elastomer.

9. The method according to claim 1 wherein the internally blocked organoborate has the structure:

wherein M is a counter ion with charge m of +1, +2, or +3.

10. The method according to claim 1 wherein the internally blocked organoborate has the structure:

wherein M is a counter ion with charge m of +1, +2, or +3.

11. The method according to claim 1 wherein the internally blocked organoborate has the structure:

wherein M is a counter ion with charge m of +1, +2, or +3.

12. The method according to claim 1 wherein the internally blocked organoborate has the structure:

wherein M is a counter ion with charge m of +1, +2, or +3.

13. The method according to claim 1 wherein the internally blocked organoborate has the structure:

wherein M is a counter ion with charge m of +1, +2, or +3.

14. The method according to claim 1 wherein the internally blocked organoborate has the structure:

wherein M is a counter ion with charge m of +1, +2, or +3.

15. The method according to claim 1 wherein the internally blocked organoborate has the structure:

wherein M is a counter ion with charge m of +1, +2, or +3.

16. The method according to claim 1 wherein the internally blocked organoborate has the structure:

wherein M is a counter ion with charge m of +1, +2, or +3.

17. The method according to claim 1 wherein the internally blocked organoborate has the structure:

wherein M is a counter ion with charge m of +1, +2, or +3.

18. The method of claim 1 wherein said mixture further comprises a polymeric material.

* * * * *